US011820568B2

(12) United States Patent
Zeeli et al.

(10) Patent No.: US 11,820,568 B2
(45) Date of Patent: Nov. 21, 2023

(54) FLUORINATED SHRINK WRAP FOR SURGICAL ITEM IDENTIFICATION TAGS

(71) Applicant: STERIS CORPORATION, Mentor, OH (US)

(72) Inventors: Dan Zeeli, North York (CA); Guy Dor, Rosh Haayn (IL); Ilan Kadosh-Tamari, Ramat Hasharon (IL)

(73) Assignee: STERIS Corporation, Mentor, OH (US)

( * ) Notice: Subject to any disclaimer, the term of this patent is extended or adjusted under 35 U.S.C. 154(b) by 0 days.

(21) Appl. No.: 17/546,083

(22) Filed: Dec. 9, 2021

(65) Prior Publication Data

US 2022/0185560 A1    Jun. 16, 2022

Related U.S. Application Data

(60) Provisional application No. 63/125,982, filed on Dec. 16, 2020.

(51) Int. Cl.
| | |
|---|---|
| *B65D 71/08* | (2006.01) |
| *B65B 53/02* | (2006.01) |
| *G09F 3/02* | (2006.01) |
| *A61B 90/90* | (2016.01) |
| *A61B 90/98* | (2016.01) |

(52) U.S. Cl.
CPC .............. *B65D 71/08* (2013.01); *A61B 90/90* (2016.02); *B65B 53/02* (2013.01); *G09F 3/02* (2013.01); *A61B 90/98* (2016.02); *G09F 2003/0251* (2013.01); *G09F 2003/0272* (2013.01)

(58) Field of Classification Search
CPC ..... G09F 2003/0272; G09F 2003/0251; G09F 3/02; A61B 90/90–98; B65B 25/00; B65B 53/06; B65B 53/02; B65B 61/20; B65D 71/08
USPC ........................... 206/210, 497; 53/585, 442
See application file for complete search history.

(56) References Cited

U.S. PATENT DOCUMENTS

| | | | | |
|---|---|---|---|---|
| 1,642,894 | A * | 9/1927 | Rober ....................... | A23G 1/20 53/514 |
| 1,875,110 | A * | 8/1932 | Myers ....................... | B65C 3/18 53/287 |
| 2,303,420 | A * | 12/1942 | Amberg ................. | A23G 9/288 53/445 |
| 2,787,104 | A * | 4/1957 | Carter ....................... | B65B 9/14 156/DIG. 15 |
| 2,976,661 | A * | 3/1961 | Bagnelle ................. | B67B 5/038 156/DIG. 15 |
| 3,286,835 | A * | 11/1966 | Crane, Jr. ............ | B65D 73/005 53/399 |
| 3,657,862 | A * | 4/1972 | Milne .................... | B65B 53/02 53/329.2 |
| 4,144,631 | A * | 3/1979 | Fujio ....................... | B29C 63/18 29/235 |

(Continued)

*Primary Examiner* — Robert F Long
*Assistant Examiner* — Eduardo R Ferrero

(57) ABSTRACT

A method of enclosing a surgical item identification tag in a fluorinated shrink wrap, including cutting one or more elongated pieces from a shrink wrap tube to form cut shrink wrap pieces, placing cut shrink wrap pieces into cavities in a tray, inserting an identification tag into each of the cut shrink wrap pieces, heating the cut shrink wrap pieces to cause the cut shrink wrap pieces to shrink and wrap around the identification tag, sealing an upper end and lower end of the cut shrink wrap pieces.

16 Claims, 3 Drawing Sheets

(56) References Cited

U.S. PATENT DOCUMENTS

| | | | | |
|---|---|---|---|---|
| 4,318,685 A * | 3/1982 | Konstantin | B65B 61/202 | 425/515 |
| 4,387,553 A * | 6/1983 | Strub | B65C 3/065 | 53/291 |
| 4,436,777 A * | 3/1984 | Karpiloff | B44C 3/087 | 429/176 |
| 4,511,416 A * | 4/1985 | Karpiloff | B44C 1/14 | 53/585 |
| 4,514,966 A * | 5/1985 | Konstantin | B65C 3/065 | 53/291 |
| 5,101,613 A * | 4/1992 | Wilhelm | B67B 5/036 | 53/295 |
| 5,650,596 A * | 7/1997 | Morris | G06M 1/108 | 177/245 |
| 6,777,623 B2 * | 8/2004 | Ballard | A61B 50/37 | 705/28 |
| 6,998,541 B2 * | 2/2006 | Morris | A61M 1/777 | 177/15 |
| 7,019,650 B2 * | 3/2006 | Volpi | G06K 7/10336 | 340/520 |
| 7,347,034 B1 * | 3/2008 | Kwon | B65B 53/063 | 53/298 |
| 7,399,899 B2 * | 7/2008 | Fabian | A61F 13/44 | 602/41 |
| 7,420,468 B2 * | 9/2008 | Fabian | A61B 5/7242 | 340/568.1 |
| 7,557,710 B2 * | 7/2009 | Sanchez | A61B 90/98 | 340/286.07 |
| 7,644,016 B2 * | 1/2010 | Nycz | G06Q 10/0875 | 705/28 |
| 7,696,877 B2 * | 4/2010 | Barnes | G08B 21/0225 | 340/657 |
| 7,755,491 B2 * | 7/2010 | Volpi | G01S 13/825 | 340/505 |
| 7,784,468 B2 * | 8/2010 | Fabian | A61B 5/06 | 340/572.1 |
| 8,177,776 B2 * | 5/2012 | Humayun | A61B 50/33 | 606/1 |
| 8,710,957 B2 * | 4/2014 | Blair | A61B 5/06 | 340/572.1 |
| 10,874,560 B2 * | 12/2020 | Merritt | A61B 90/90 | |
| 2002/0176730 A1 * | 11/2002 | Bleckmann | B29C 53/36 | 400/615.2 |
| 2003/0036771 A1 * | 2/2003 | McEwen | A61B 17/1355 | 606/202 |
| 2004/0016207 A1 * | 1/2004 | Lortz | B65B 19/34 | 53/397 |
| 2004/0146698 A1 * | 7/2004 | Pace | B41F 17/001 | 428/199 |
| 2006/0043179 A1 * | 3/2006 | Nycz | A61B 50/33 | 235/385 |
| 2006/0244593 A1 * | 11/2006 | Nycz | A61B 90/98 | 340/572.1 |
| 2006/0244652 A1 * | 11/2006 | Tethrake | A61B 90/98 | 342/44 |
| 2007/0268133 A1 * | 11/2007 | Sanchez | G08B 13/2462 | 340/568.1 |
| 2009/0139891 A1 * | 6/2009 | Oshima | B32B 38/145 | 428/32.22 |
| 2009/0272806 A1 * | 11/2009 | Kemp | B23K 26/355 | 235/492 |
| 2010/0035027 A1 * | 2/2010 | Hill | G09F 21/02 | 156/60 |
| 2010/0201487 A1 * | 8/2010 | Halberthal | H01Q 7/00 | 343/702 |
| 2010/0273698 A1 * | 10/2010 | Noding | B65B 49/06 | 53/436 |
| 2012/0040113 A1 * | 2/2012 | Sato | B41M 7/00 | 428/34.1 |
| 2012/0058046 A1 * | 3/2012 | Sugimoto | H01M 8/04208 | 53/442 |
| 2012/0212330 A1 * | 8/2012 | Halberthal | H01Q 7/00 | 343/742 |
| 2013/0287323 A1 * | 10/2013 | Slovut | B65D 33/1658 | 53/482 |
| 2014/0053509 A1 * | 2/2014 | Henderson | B32B 27/06 | 53/442 |
| 2015/0062504 A1 * | 3/2015 | Hoshino | G03H 1/0244 | 349/98 |
| 2015/0149330 A1 * | 5/2015 | Sweeney | G06Q 10/087 | 705/28 |
| 2016/0058510 A1 * | 3/2016 | Blice | B32B 3/06 | 206/363 |
| 2016/0104395 A1 * | 4/2016 | Klein | G09F 3/16 | 40/637 |
| 2016/0371574 A1 * | 12/2016 | Nguyen | G06K 17/0022 | |
| 2017/0202630 A1 * | 7/2017 | Gerstner | A61B 50/13 | |
| 2018/0098822 A1 * | 4/2018 | Bilsøe | A61B 90/98 | |
| 2020/0002042 A1 * | 1/2020 | Christman | B65B 21/245 | |

* cited by examiner

FLUORINATED SHRINK WRAP FOR SURGICAL ITEM IDENTIFICATION TAGS

TECHNICAL FIELD

The present invention relates to protection of identification tags used with surgical items and more specifically to protecting the tag with a fluorinated shrink wrap.

BACKGROUND

An operation room is a facility in which intrusive operations are performed on patients. Typically, multiple people participate in an operation, including a chief surgeon, an assistant surgeon, an anesthesiologist, a scrub nurse, and a circulating nurse. The participating personnel use multiple surgical items and disposable items, varying according to the surgery being performed.

Intensive efforts are invested in keeping track of all surgical items and disposables, in order to make sure no item unintentionally remains inside the patient's body. Therefore careful counting is performed before during and after the operation.

Counting the surgical items is a tedious job and requires intensive resources, including mental resources, personnel time and down-time of the operating room. Counting the surgical items towards the end of an operation also increases the time the patient's body is open with the associated risks.

In addition, counting is not always error-free, and in some cases surgical items end up being left within the patient's body, causing severe damage and even death.

A solution to this problem is provided by attaching identification tugs to the surgical items (tools and disposables) so that the surgical items may be located, counted and tracked by computerized systems.

The tags and disposables are used in non-sterile environments. The tags come in contact with blood and other fluids and may be cleaned and/or sterilized while attached to surgical items. Additionally, the tags are constantly in friction with other elements, such as medical devices, body parts and/or other surgical items. Thus the tags need to be protected to prevent them from being damaged and malfunctioning during use.

One solution previously used was to encapsulate the tags in an epoxy mold. However this process places a burden on the manufacturing process consuming a lot of time until the mold is cured and using up a lot of space to store the molds while being cured. Not to mention the consumption of energy that may be required to heat the molds. Likewise epoxy mold encapsulation increases the size of the final product, making the tag more bulky. Thus increasing the probability that the tag will interfere with surgical procedures.

SUMMARY

An aspect of an embodiment of the disclosure relates to an identification tag for identifying surgical items, wherein the identification tag is enclosed within a protective shrink wrap tube made from a fluorinated polymer that shrinks to tightly enclose around the identification tag when heat is applied. The shrink wrap is elongated with two ends, an upper end and a lower end, that are sealed to prevent moisture from entering the shrink wrap. Optionally, the ends are smoothed to remove sharp edges and prevent damage.

In an embodiment of the disclosure, a roll of shrink wrap tubing that is made from a fluorinated polymer is used to enclose the identification tags. The roll is cut into a preselected number of elongated pieces matching a number of cavities in a tray. Each piece is cut large enough to accommodate an identification tag. Each cut piece is inserted into one of the cavities of the tray. Then the identification tag is inserted into the shrink wrap and heated to cause the shrink wrap to shrink and tightly enclose around the identification tag. After shrinking the shrink wrap the ends are sealed so that the identification tag is protected from moisture and dust. There is thus provided according to an embodiment of the disclosure, a method of enclosing a surgical item identification tag in a fluorinated shrink wrap, comprising:

Cutting one or more elongated pieces from a shrink wrap tube to form cut shrink wrap pieces;
Placing cut shrink wrap pieces into cavities in a tray;
Inserting an identification tag into each of the cut shrink wrap pieces;
Heating the cut shrink wrap pieces to cause the cut shrink wrap pieces to shrink and wrap around the identification tag;
Sealing an upper end and lower end of the cut shrink wrap pieces.

In an embodiment of the disclosure, the roll of shrink wrap is cut into a preselected number of equal sized pieces before said placing. Optionally, the preselected number is selected to match the number of cavities in the tray. In an embodiment of the disclosure, each of the cut shrink wrap pieces is large enough to completely enclose the identification tag. Optionally, each of the cavities in the tray has a stopper protruding from the bottom, configured so that each of the cut shrink wrap pieces will slide onto the stopper and the stopper will hold the cut shrink wrap piece open so that an identification tag can slide into the cut shrink wrap piece and be positioned at about a center of a length of the cut shrink wrap piece. In an embodiment of the disclosure, the sealing is performed by grasping each of the upper end and lower end of the cut shrink wrap piece and melting the respective end. Optionally, the sealed upper end and lower end are filed down to remove sharp edges. In an embodiment of the disclosure, the enclosed identification tag is attached to a disposable item by sewing the identification tag into a small pouch that is formed from the disposable item. Optionally, the enclosed identification tag is attached to a disposable item by sewing the identification tag into a small pouch that is attached to the disposable item. In an embodiment of the disclosure, the fluorinated shrink wrap is manufactured without toxic anti-flammable chemicals.

There is further provided according to an exemplary embodiment of the disclosure, a surgical item identification tang enclosed by a fluorinated shrink wrap, comprising:

A shrink wrap in the form of an elongated cut piece of a shrink wrap tube that was heated to shrink forming a wrap around the identification tag;
Wherein the cut shrink wrap piece includes an upper end and a lower end that were sealed to entirely enclose the shrink wrap.

In an embodiment of the disclosure, the fluorinated shrink wrap does not include toxic anti-flammable chemicals. Optionally, the sealed upper end and lower end are filed down to remove sharp edges.

BRIEF DESCRIPTION OF THE DRAWINGS

The present disclosure will be understood and better appreciated from the following detailed description taken in conjunction with the drawings. Identical structures, elements or parts, which appear in more than one figure, are generally labeled with the same or similar number in all the figures in which they appear. It should be noted that the elements or parts in the figures are not necessarily shown to scale and each elements or part may be larger or smaller than actually shown.

DETAILED DESCRIPTION

Figure 1:
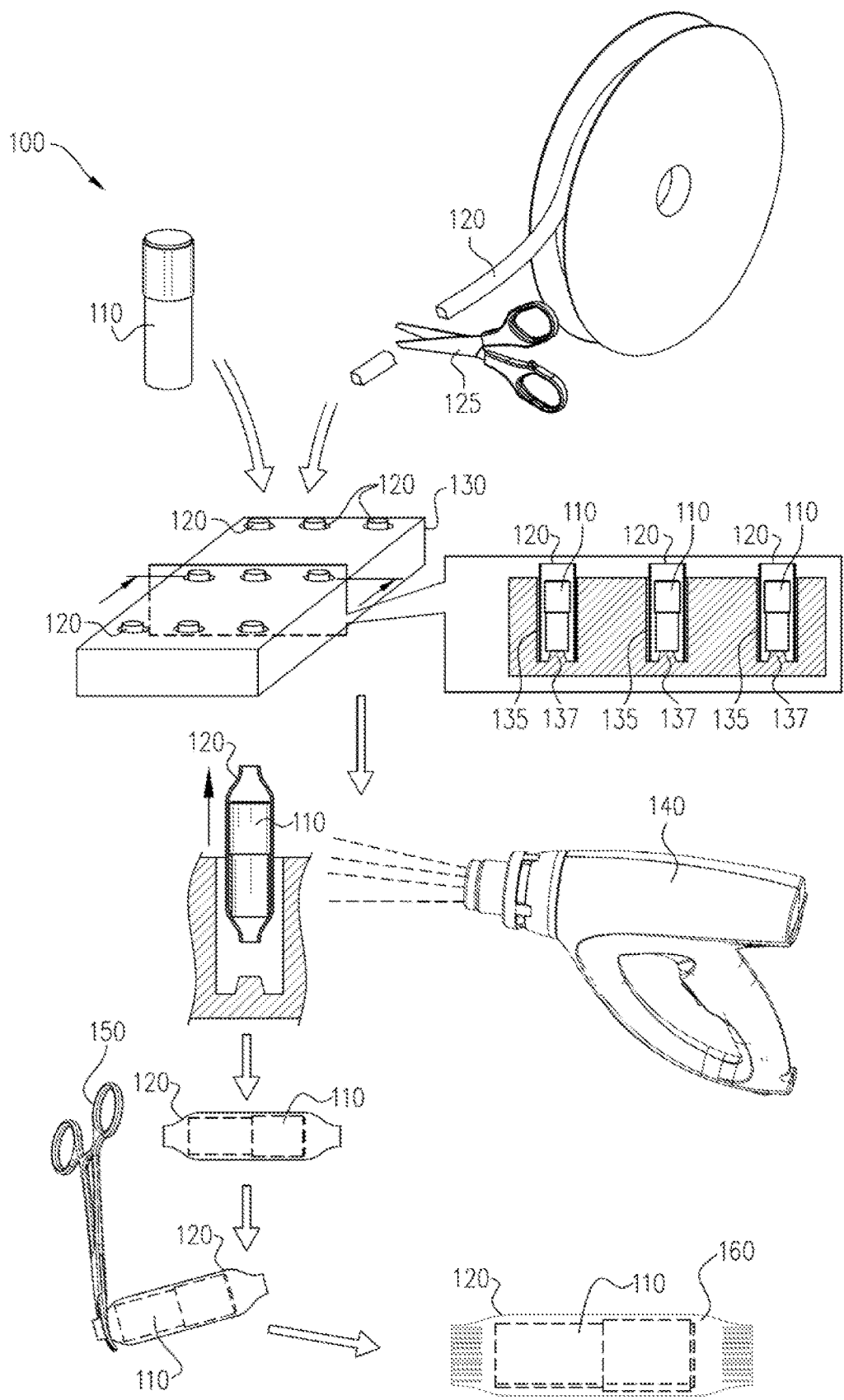
FIG. 1 is a schematic illustration of a process of wrapping a tag with a fluorinated shrink wrap, according to an embodiment of the disclosure.
Figure 2:
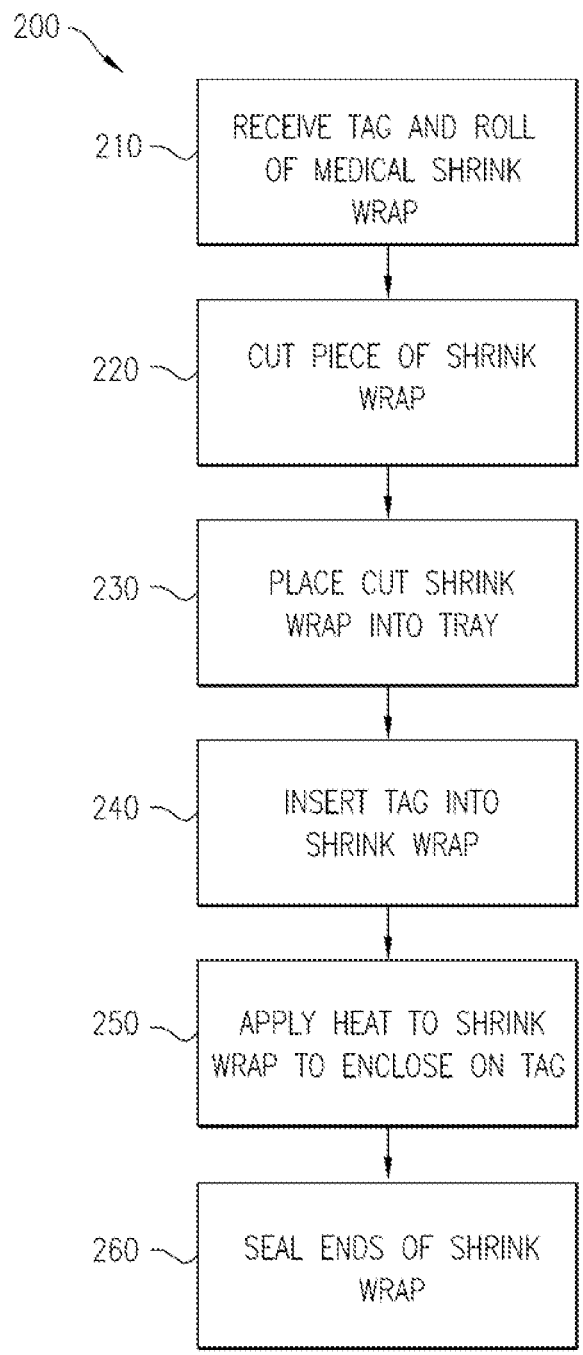
FIG. 2 is a flow diagram of a process of wrapping a tag with a fluorinated shrink wrap, according to an embodiment of the disclosure.
Figure 3:
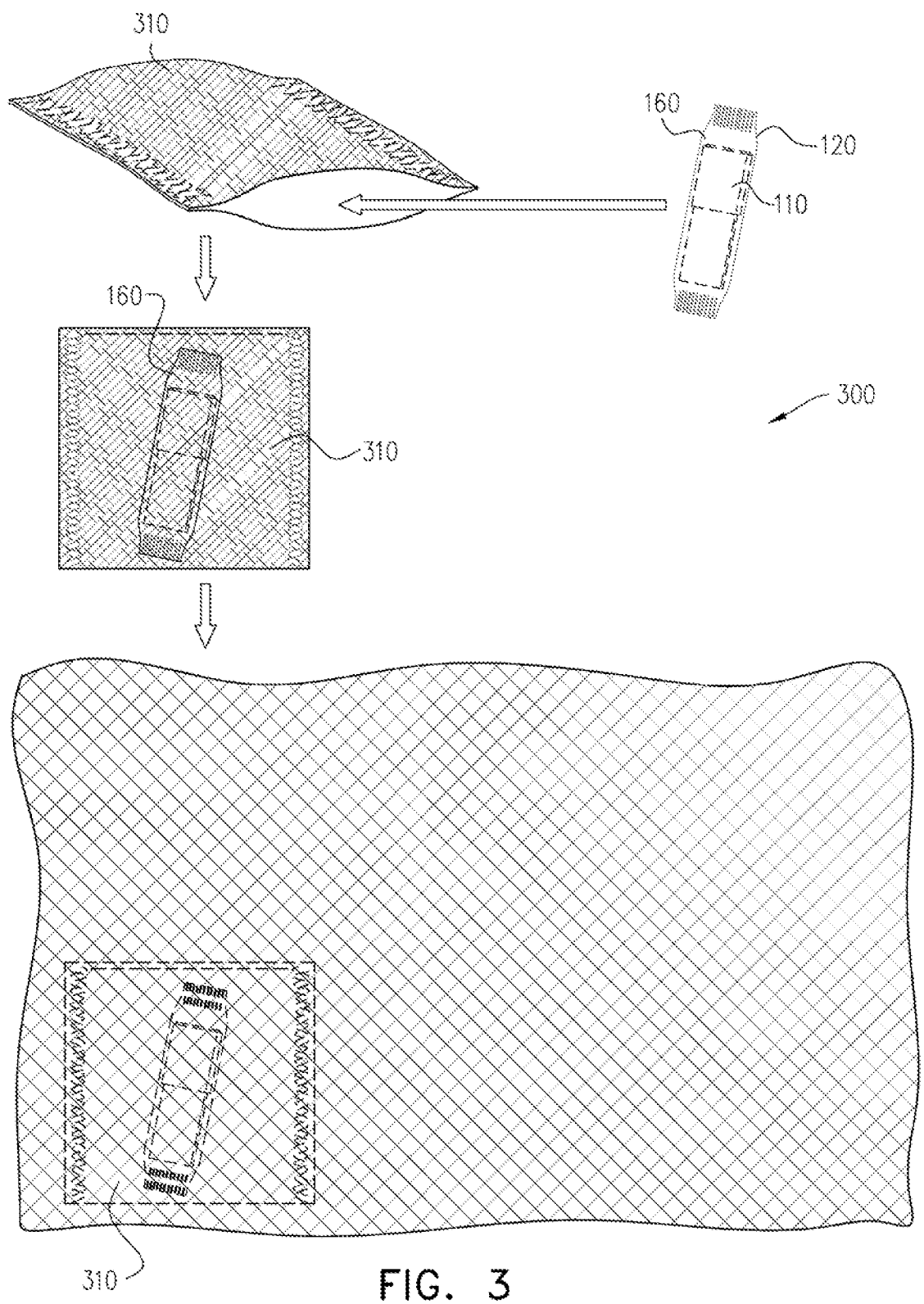
FIG. 3 is a schematic illustration of a surgical item with a shrink wrapped tag attached, according to an embodiment of the disclosure.

FIG. 1 is a schematic illustration of a process 100 of wrapping tag 110 with the fluorinated shrink wrap 120, FIG. 2 is a flow diagram of a process 200 of wrapping tag 110 with fluorinated shrink wrap 120, and FIG. 3 is a schematic illustration of a surgical item 300 with a shrink wrapped tag 160 attached, according to an embodiment of the disclosure. Optionally, process 200 is the same or similar as process 100, but one of the processes may disclose options, which are not mentioned by the other rendering them distinct.

In an embodiment of the disclosure, an identification tag 110 (e.g. an RFID tag) is used to track and identify surgical items 300, such as tools (e.g. forceps and scissors) and disposables (e.g. sponges, cloths and towels). The tag 110 is wrapped in a fluorinated shrink wrap 120 to protect it from friction, moisture, dirt or other damage, which may render the tag 110 unresponsive. The shrink wrap 120 is then attached to the surgical items 300 (e.g. a towel or cloth as shown in FIG. 3) to enable tracking the surgical items 300 with a computerized system.

In an embodiment of the disclosure, one or more tags 110 and a roll of shrink wrap 120 (e.g. a PVDF (polyvinylidene fluoride) medical grade shrink tube made from a fluoropolymer) are received (210) by a manufacturer or user for attaching to medical elements 300 (FIG. 3). The user cuts (220) a piece of shrink wrap 120, for example with a pair of scissors 125 or by an automated cutting machine as part of an automated production line The size of the shrink wrap is selected to match the size of the tag 110 that is to be wrapped. In an exemplary embodiment, the tag may be cylindrical or planar with a diameter/width of about 4-7 mm, and height/length of about 10-15 mm. Optionally, the cut piece of shrink wrap 120 will have a diameter of about 5-8 mm and height of about 15-20 mm to accommodate the tag 110.

In an embodiment of the disclosure, the cut piece of shrink wrap 120 is placed (230) in a tray 130 having cavities 135 (e.g. cylindrical cavities) for accommodating the shrink wrap 120 and the tag 110. Optionally, the roll of shrink wrap 120 is cut into a preselected number of pieces, for example one piece for each cavity 135 of the tray 130.

In an embodiment of the disclosure, the cavities 135 are configured in size to accommodate an open piece of shrink wrap 120, so that the tag may be easily inserted within. In an embodiment of the disclosure, a stopper 137 is positioned at the bottom of the cavity, for example a cylindrical column where the shrink wrap 120 slides onto the stopper. The shrink wrap 120 is then held open by the stopper 137, so that the tag 110 can slide into the shrink wrap 120 and the stopper will position the tag 110 at about the center of the length of the shrink wrap 120.

In an embodiment of the disclosure, the user inserts (240) the tag 110 into the shrink wrap 120 that is placed in the cavity 135 in the tray 130, so that the tag 110 is located approximately at the center of the length of the cut out piece of shrink wrap 120. Optionally, heat is applied (250) to the shrink wrap 120 causing it to shrink and wrap around the tag 110. Heat may be applied (250) by using a heat blower 140, or an automated heat generating apparatus, at a temperature of about 150-200° C. for a few minutes to each cavity 135 of the tray 130 with a shrink wrap 120 and tag 110 inserted therein. Optionally, the shrink wrap 120 tightly encloses over the tag 110, so that the size of the resulting shrink wrapped tag 160 is about the same as the original tag 110 in contrast to a tag that is encapsulated by epoxy or other molding procedures, which is generally much larger.

In an embodiment of the disclosure, an end of the shrink wrap 120 enclosing on tag 110 is grasped with a tool such as toothed forceps 150 for a better grasp or any other tool that can apply force. The end is then heated, for example up to about 200-240° C. to melt the end of the shrink wrap 120 and seal (260) the end. The same process is applied to the other end, so that the resulting shrink wrapped tag 160 will be completely sealed (260) within the shrink wrap 120 and be liquid proof. In some embodiments of the disclosure, both ends can be sealed in one step using tools that will be applied on both ends simultaneously, while applying force and heated up to 200-240° C. to reach the material inciting point of the shrink wrap 120.

Alternatively, the ends may be sealed by other methods, such as by ultrasonic welding, heat lamination, resistance heating, electrofusion, infrared heating, RF heating or magnetic field heating.

In an embodiment of the disclosure, the ends of the shrink wrap 120 are melted or filed down, so that the final product does not have sharp edges, which could be dangerous for the user.

Shrink wrap 120 provides a low cost protective encasement for tags 110. The shrink wrap 120 is especially useful for tags 110 that are used on disposable surgical items 300 (e.g. FIG. 3), since it is cheaper than molding an epoxy enclosure and curing it. The fluoropolymer material of the shrink wrap 120 shrinks in size when heated to wrap around the tag 110, thus it can be used to tightly encapsulate tags 110. The shrink wrap 120 serves as a protective padding for the tag 110 that protects the tag 110 from physical damage, which may be caused by rubbing against other materials, collisions or other forces. Likewise the shrink wrap 120 also provides heat insulation, electrical insulation and protection from liquids.

In some embodiments of the disclosure, the fluoropolymer tubing is manufactured without the use of anti-flammable chemicals, which are toxic and not recommended for use in medical applications. Thus this component is removed from the composition that is used to form the roll of shrink wrap 120.

In an embodiment of the disclosure, the shrink wrapped tag 160 is attached to the surgical item 300 (e.g. a gauze pad, cloth or towel) by being sewn into a small pouch 310 that is either a part of the disposable item or sewn on to the disposable item (FIG. 3).

In the case of a tool the shrink wrapped tag 160 may be attached by an adhesive or wires or placed in a predesigned compartment that is part of the tool. Alternatively, the shrink wrapped tag 160 may be embedded into the surgical tool during the manufacturing process of the tool.

It should be appreciated that the above described methods and apparatus may be varied in many ways, including omitting or adding steps, changing the order of steps and the type of devices used. It should be appreciated that different features may be combined in different ways. In particular, not all the features shown above in a particular embodiment are necessary in every embodiment of the disclosure. Further combinations of the above features are also considered to be within the scope of some embodiments of the disclosure. It will also be appreciated by persons skilled in the art that the present disclosure is not limited to what has been particularly shown and described hereinabove but rather also applicable to equivalents and obvious variations.

We claim:

1. A method of enclosing a surgical item identification tag in a fluorinated shrink wrap, comprising:
   cutting one or more elongated pieces from a shrink wrap tube to form cut shrink wrap pieces;
   placing cut shrink wrap pieces into cavities in a tray, wherein each of the cavities in the tray includes a stopper protruding configured so that each of the cut shrink wrap pieces slides onto the stopper and the stopper holds the cut shrink wrap pieces open;
   inserting an identification tag into each of the cut shrink wrap pieces wherein the stopper positions the identification tag at about the center of a length of the cut shrink wrap piece;
   heating the cut shrink wrap pieces to cause the cut shrink wrap pieces to shrink and wrap around the identification tag;
   sealing an upper end and lower end of the cut shrink wrap pieces.

2. The method of claim 1, wherein the roll of shrink wrap is cut into a preselected number of equal sized pieces before said placing.

3. The method of claim 2, wherein the preselected number is selected to match the number of cavities in the tray.

4. The method of claim 1, wherein each of the cut shrink wrap pieces is large enough to completely enclose the identification tag.

5. The method of claim 1, wherein the sealing is performed by grasping each of the upper end and lower end of the cut shrink wrap piece and inciting the respective end.

6. The method of claim 1, wherein the sealed upper end and lower end are filed down to remove sharp edges.

7. The method of claim 1, wherein the enclosed identification tag is attached to a disposable item by sewing the identification tag into a small pouch that is formed from the disposable item.

8. The method of claim 1, wherein the enclosed identification tag is attached to a disposable item by sewing the identification tag into a small pouch that is attached to the disposable item.

9. The method of claim 1, wherein the fluorinated shrink wrap is manufactured without toxic anti-flammable chemicals.

10. The method of claim 1, wherein the cavities are cylindrical in shape and the stopper is a cylindrical column.

11. A method of enclosing a surgical item identification tag in a fluorinated shrink wrap, comprising:
    cutting one or more elongated pieces from a shrink wrap tube to form cut shrink wrap pieces into a preselected number of equal sized pieces, wherein the fluorinated shrink wrap is manufactured without toxic anti-flammable chemicals;
    placing cut shrink wrap pieces into cavities in a tray wherein the preselected number is selected to match the number of cavities in the tray, wherein each of the cavities in the tray includes a stopper protruding configured so that each of the cut shrink wrap pieces slides onto the stopper and the stopper holds the cut shrink wrap pieces open;
    inserting an identification tag into each of the cut shrink wrap pieces wherein the stopper positions the identification tag at about the center of a length of the cut shrink wrap piece;
    heating the cut shrink wrap pieces to cause the cut shrink wrap pieces to shrink and wrap around the identification tag;
    sealing an upper end and lower end of the cut shrink wrap pieces.

12. The method of claim 11, wherein each of the cut shrink wrap pieces is large enough to completely enclose the identification tag.

13. The method of claim 11, wherein the sealing is performed by grasping each of the upper end and lower end of the cut shrink wrap piece and melting the respective end.

14. The method of claim 11, wherein the sealed upper end and lower end are filed down to remove sharp edges.

15. The method of claim 11, wherein the enclosed identification tag is attached to a disposable item by sewing the identification tag into a small pouch that is formed from the disposable item.

16. The method of claim 11, wherein the enclosed identification tag is attached to a disposable item by sewing the identification tag into a small pouch that is attached to the disposable item.

* * * * *